(12) United States Patent
Horres et al.

(10) Patent No.: US 8,916,227 B2
(45) Date of Patent: Dec. 23, 2014

(54) COATING OF THE ENTIRE SURFACE OF ENDOPROSTHESES

(75) Inventors: Roland Horres, Stolberg (DE); Michael Hoffmann, Eschweiler (DE); Erika Hoffmann, Eschweiler (DE); Marita Linssen, Aachen (DE); Roger Caspers, Inden (DE); Michaela Styrnik, Eschweiler (DE)

(73) Assignee: Hemoteq AG, Wurselen (DE)

( * ) Notice: Subject to any disclaimer, the term of this patent is extended or adjusted under 35 U.S.C. 154(b) by 2076 days.

(21) Appl. No.: 11/913,545

(22) PCT Filed: May 3, 2006

(86) PCT No.: PCT/DE2006/000766
§ 371 (c)(1),
(2), (4) Date: Nov. 2, 2007

(87) PCT Pub. No.: WO2006/116989
PCT Pub. Date: Nov. 9, 2006

(65) Prior Publication Data
US 2008/0199506 A1 Aug. 21, 2008

Related U.S. Application Data

(60) Provisional application No. 60/687,340, filed on Jun. 6, 2005.

(30) Foreign Application Priority Data

May 5, 2005 (DE) .......................... 10 2005 021 622

(51) Int. Cl.
| A61L 33/00 | (2006.01) |
|---|---|
| C09D 5/14 | (2006.01) |
| A61L 27/34 | (2006.01) |
| A61L 27/54 | (2006.01) |
| A61L 29/08 | (2006.01) |
| A61L 29/16 | (2006.01) |
| A61L 31/10 | (2006.01) |
| A61L 31/16 | (2006.01) |

(52) U.S. Cl.
CPC . *C09D 5/14* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61L 2300/606* (2013.01); *A61L 2420/02* (2013.01)
USPC .......................... 427/2.24; 623/1.11; 514/449

(58) Field of Classification Search
USPC ......................................... 514/449; 623/1.11
See application file for complete search history.

(56) References Cited

U.S. PATENT DOCUMENTS

| 5,876,448 A | 3/1999 | Thompson et al. |
|---|---|---|
| 5,951,599 A | 9/1999 | McCrory |
| 5,977,163 A * | 11/1999 | Li et al. .......................... 514/449 |
| 6,702,850 B1 | 3/2004 | Byun et al. .................... 623/1.44 |
| 2002/0138127 A1 * | 9/2002 | Stiger et al. .................. 623/1.11 |

FOREIGN PATENT DOCUMENTS

| KR | 10-2004-0028486 | | 4/2004 |
|---|---|---|---|
| WO | WO2005/032611 | | 4/2001 |
| WO | 02/24249 | | 3/2002 |
| WO | WO 02/24249 | | 3/2002 |
| WO | 2005/030086 | | 4/2005 |
| WO | 2005/032611 | | 4/2005 |
| WO | WO 2005/030086 | * | 4/2005 |
| WO | WO 2005/030094 | | 4/2005 |

OTHER PUBLICATIONS

Chinese First Examination Report of China Patent Application No. 2006800152027, dated Jan. 29, 2010.
Korean Examination Report of Korea Application No. 10-2007-7026769, dated May 15, 2009.
International Search Report of International Application No. PCT/DE2006/000766, dated Aug. 10, 2007.

* cited by examiner

*Primary Examiner* — Dah-Wei D Yuan
*Assistant Examiner* — Andrew Bowman
(74) *Attorney, Agent, or Firm* — J.C. Patents

(57) ABSTRACT

The present invention relates to methods for coating the entire surface of lattice-like or mesh-like endoprostheses, wherein the endoprostheses initially are being provided with a thin layer covering the material surface of the endoprosthesis and subsequently, the surface of the entire endoprosthesis is being coated, wherein said coating of the entire surface covers the struts as well as the interstices between the individual struts.

34 Claims, No Drawings

COATING OF THE ENTIRE SURFACE OF ENDOPROSTHESES

CROSS-REFERENCE TO RELATED APPLICATION

This application is a 371 application of an International PCT application no. PCT/DE2006/000766, filed on May 3, 2006, which claims the priority benefit of German application no. 10 2005 021 622.6, filed on May 5, 2005 and U.S. provisional application Ser. No. 60/687,340, filed on Jun. 6, 2005. The entirety of each of the above-mentioned patent applications is hereby incorporated by reference herein and made a part of this specification.

The present invention relates to methods for coating the entire surfaces of lattice-like or mesh-like endoprostheses, wherein the endoprosthesis is initially being provided with a thin layer covering the material surface of the endoprosthesis, i.e. the struts forming the lattice or mesh, and the entire or respectively a continuous surface area of the endoprosthesis is subsequently being coated, wherein said coating of the entire or respectively of a continuous surface area covers the struts as well as the interstices between the individual struts.

Pathological alterations concerning any body passageway can lead to constriction or even total occlusion of the same. Arteriosclerosis, as well as acute thrombosis, are a frequent cause for conditions such as myocardial infarction or respectively apoplectic stroke.

Another frequently occurring risk regarding body passageways is malign and benign tumor growth. Due to fast and uncontrolled cell division the tumor spreads in areas adjacent to and within hollow organs and thus obstructs or respectively occludes the affected body passageways. Esophageal cancer, colon cancer, lung cancer, kidney cancer, occlusion of the biliary tract, the pancreas and the urethra can be cited as examples of such conditions.

During the last two decades, stents have proven to be suitable local therapy methods for the treatment of constricted blood vessels. After having dilated the affected site by means of a balloon catheter, or even after having removed the constricted portion, the stent is placed at the affected site, where it is expanded and thus dilates the vascular wall to such a degree that the original diameter of the affected vessel is restored and the vessel is kept open.

In particular in the case of stents getting in contact with blood said stents, as an exogenous material, cause the formation of restenoses. Efforts made in the development of stents aiming at providing an improved biocompatibility of the stent material, a higher flexibility combined with reduced material fatigue and a reduction of the foreign surface are intended to further minimize the rate of stent-induced restenosis.

Coating of the stent surface with biocompatible, biodegradable or biostable materials serving as carriers for an anti-restenotic active agent has proven to be a promising improved development when added to the above-cited basic requirements to be fulfilled by the stent body. Said active agent is supposed to stop the restenosis-promoting process by means of a release adapted to the requirements in terms of time and concentration. The requirements to be met by the stent as such as well as by the coating material, the coating quality and the active agents are similarly high.

The same basic body is used for preventing or interfering with e.g. constrictions caused by tumor growth in the esophagus or in the bronchial trachea. Contrary to the vascular stent for treating arteriosclerosis, these stents are provided with a polymer coat covering the stent body which, due to its function as mechanical barrier, is supposed to prevent or at least reduce reoccurring tumor ingrowth into the lumen through the interstices.

A characteristic feature common to all foreign materials inserted into body lumens consists in the fact that said materials are supposed to ensure, if possible, an unlimited flexibility, that is the physiologically necessary free motility of the target organ while eliminating or retarding local conditions impairing the normal function of the lumen. Said flexibility depends on the material and design of the hollow body and has led to a hollow body covering a relatively small area of the vascular wall and having a wide-meshed or respectively mesh-like structure.

Different requirements concerning the characteristic features of the implant are to be considered depending on the clinical characteristics of the disease and the application site. Thus, for example the requirements concerning an endoprosthesis inserted into an artery differ from those to be met by an endoprosthesis inserted into the esophagus. A stent can only be used as a barrier in the treatment of a tumor if it is capable of entirely covering the affected area, whereas the foreign surface of both coated and uncoated vascular stents should be as limited as possible for preventing stent-induced restenosis. The former is only possible if the large interstices, which are typical for stents, do not remain permeable and are able to inhibit tumor growth. This is achieved by means of a polymer shell surrounding the endoprosthesis.

However, whereas for a vascular stent, the most important requirement is a hemocompatible surface, in the case of an esophagus stent it is in contrast a compulsory requirement that the stent be securely attached in a manner that prevents it from slipping into the stomach due to the peristalsis of swallowing. The material of the endoprosthesis as well of that of the polymer shell should furthermore have a certain resistance to gastric acid (reflux, vomiting).

Obviously, the stent to be placed in the trachea must not impair respiration, and the polymer shell may not obstruct the drainage of mucus and secretion. Furthermore, it has to dispose of a certain resistance to the high pressures and air velocities which occur during sneezing and coughing. Concerning the renal tract, the urethra or for example the biliary tract, other requirements depending on the respective environment have to be met.

Depending on the site of application, it is possibly necessary to differentiate the surface structure of such medical device between the outer surface and the inner surface facing the lumen.

Since the stent which is covered with polymer is supposed to fulfill its function in a manner which is adapted to the respective site and which, in the ideal case, is supposed to provide for or respectively support the function of the target organ without disturbing or impairing its function, different concepts aiming at providing a stent with a polymer shell were prepared.

However, the application of stents for the nonvascular application is not yet established.

Thus, U.S. Pat. No. 5,876,448 (WO 93/22986) describes a self-expanding esophageal stent provided with a silicone tube along the medial region of said stent, which tube compresses the stent such that it has a smaller diameter than in the proximal and distal end portions which are not covered by the tube. The proximal and distal ends are not covered so as to provide for an improved fixation on the walls of the cavity by means of these free stent struts. However, this stent has not proven itself successful, since the compression of the stent body leads to problems, such as the fact that the forces applied on the stent during vomiting are increased in a manner that causes the stent to be moved and to possibly cause injuries on the esophageal wall with its free end.

Moreover, the silicone tube could be torn or respectively be detached under these circumstances, mucus or food particles could be deposited between the vascular wall and the silicone coating layer, which besides the possible risk of inflammation could lead to various extremely negative effects for the patient.

WO 2005/030086 also describes a method of completely coating the surfaces of self-expanding stent bodies having a polyurethane shell, wherein the polymer is applied in the form of a film on the inner surface of the struts by means of a balloon or another appropriate hollow mold subsequent to a first spray coating of the stent with the polymer. Said method includes the fact that the coating which completely covers the surface of the stent is applied on the luminal side so that the stent struts can securely fix the stent in the vascular wall on the outer surface. The subsequent heating of the system to a temperature higher than the softening point serves for annealing the polyurethane to the stent. Herein the problem resides in the fact that the polymer shell is not bound quantitatively to the coated stent and therefore will not permanently remain attached to the stent under the given circumstances. Additionally, heating can cause small holes, which could possibly increase during the implantation and finally lead to the detachment of the coating material and even to the delocalization of the entire stent.

Furthermore, heating to a temperature above the softening point of the polymer could lead to, on the one hand, the spray coating being also present on the outer surface of the stent struts and on the other hand, to the polymer layer not only adhering to the stent but also to the balloon, which also consists of polymer. Thus, withdrawal of the balloon will cause adhesion problems since the inner coating layer is at least partially detached upon removal of the balloon from the stent. Thus, food particles or respectively mucus might deposit between the detaching coating and the inner wall, which separates the coating layer from the stent and first of all impairs the patency of the passageway. The detaching material projects into the vessel and additionally causes irritations, nausea and coughing and thus additionally promotes the defixation of the stent in total.

As for the coating, the ends of the stents are particularly problematic areas, since the first holes in the coating will be formed in most cases in these areas due to the fact that the ends of the stent struts are penetrate the covering layer. In addition to the possible injuries caused to the vascular wall, this also facilitates further detachment of the coating.

U.S. Pat. No. 5,951,599 describes an example of a stent which is completely coated on a partial surface thereof. The stent described therein is supposed to be employed in the treatment of aneurysms within blood vessels. Aneurysms are abnormal dilations of the vascular wall, in which blood accumulates and coagulates, thus increasing the dilation of the vessel. Thereby, the risk of thrombosis is increased and it finally leads to vessel rupture. U.S. Pat. No. 5,951,599 attempts to deal with this problem by filling the free interstices of a vascular stent with a small-meshed polymer network which is disposed above the site of the dilation in the blood vessel and covers the aneurysm such that the blood flow within the dilation site stagnates. As a consequence of the flow interruption, a solid thrombus is formed, which in turn stops the growth of the aneurysm. Moreover, the polymer covering layer is supposed to prevent the blood bulge or parts of the blood clot from being flushed into the blood circulation and thus, from causing an infarction in other sites. Problems inherent to poor adhesion are also occurring and deteriorate the function of the stent and thus lead to an increased risk for the patient. At present, aneurysms are still treated by being filled with metal wire ("coils"), which are supposed to stop the blood flow within the dilation site.

The present invention aims at providing an implant avoiding the described disadvantages as well as at providing an optimized method for manufacturing such implants.

Said aim is achieved by the technical teaching of the independent claims of the present invention. Further advantageous embodiments of the invention are described in the dependent claims, the description and the examples.

It has been found that the problems of the prior art can be solved by applying a first subjacent layer on the struts of the endoprosthesis, said layer not covering the interstices between the struts or respectively in the surface of the endoprosthesis, and by subsequently applying the layer which is supposed to cover the interstices within the surface or respectively between the individual struts of the endoprosthesis thus generating a tubular structure with an at least partially continuous surface area from the lattice-shaped or respectively mesh-shaped structure of the endoprosthesis, wherein the two layers form a non separable unit at the contact points of both polymer layers surrounding the individual struts of the endoprosthesis.

Thus, endoprostheses for body passageways are applied for the coating, which body passageways are generally referred to as "vessels" in the present application, for example blood vessels, veins, the esophagus, biliary tracts, renal tracts, the trachea, bronchial tubes, segments of the small intestine, large intestine or other approximately tubular body passageways, said endoprosthesis having a lattice-shaped or mesh-shaped structure, such as a stent. The term "body passageways" not only comprises natural body passageways or body lumens but also artificial body openings and body lumens such as bypasses or ileostomies. Further applications for endoprostheses coated according to the invention therefore are e.g. larynx implants, bypasses, catheters or ileostomies and in general any region in or of the living organism where an unobstructed body lumen with sufficient motility which at the same time maintains an optimal vascular wall supply, yet however minimizes the impact of the implanted foreign body on the surroundings, is important.

An endoprosthesis such as a stent does not form a solid tube but is composed of a meshed network. If a stent is examined in detail, said stent is cut e.g. by means of a laser from a solid tube, such that individual, interconnected struts are formed. The term "struts" as used in the present application refers to the individual solid segments (stent struts) of the stent scaffolding, which are interconnected at certain intersection points and form the expandable and flexible structure of the endoprosthesis.

For cutting the stent, segments between the individual struts, herein referred to as "interstices", are cut out. Therefore, an endoprosthesis has a plurality of solid scaffolding elements (e.g. struts, rings, helices, wires and intersection points), which together form the endoprosthesis, as well as a plurality of interstices between said solid elements such as intersection points and struts. In the current embodiment of endoprostheses, the struts meet at intersection points, such that the interstices are defined by the surrounding struts and intersection points. However, there are also embodiments of endoprostheses without or virtually without any intersection points and the struts e.g. have the form of rings or spirals. In the case of some of such endoprostheses only few or only one interstice, which is for example defined by two merged helices, are/is still present in lieu of the plurality of interstices. Such interstices in some cases are not clearly defined but can instead have one or two or even more open ends or open sides. Anyhow, the term "interstices" as used herein refers to the open or limited area between the solid elements of the endoprosthesis.

The present invention discloses coating methods which on the one hand allow for the increase of the surface of the endoprosthesis, which can be used for the release of the pharmacological agent so that a higher amount of said agent can be incorporated into and uniformly applied onto an increased surface area of the vessel without the need to apply a thick coating layer on the individual struts. Moreover, the coating methods according to the invention allow for the provision of completely coated surfaces of endoprostheses for certain applications such as maintaining the patency of body passageways which risk to be obstructed by tumors, said endoprostheses being able to keep the vessel permanently open while being at the same time sufficiently flexible for expansion.

This aim was achieved by completely covering the surface of the lattice-shaped or respectively mesh-like scaffolding of the endoprosthesis. The term "coating the entire surfaces" as used herein refers to a coating which covers the entire surfaces of the interstices. Said coating can also be described as a continuous coating layer, i.e., a film is formed on an interstice, wherein said film only abuts the struts defining said interstice. Said coating extends over the interstice like a suspension bridge, which is only attached on its extremities and does not abut a solid ground in the interstice. For ensuring that this coating layer, which covers the entire surface, sufficiently adheres to the struts or respectively the endoprosthesis, the struts are being at least partially coated with a polymer in a first coating step, the interstices, though, are not covered, and after wetting or respectively partially dissolving this first polymer coating layer, the step of completely coating the surface with a polymer B follows in a second coating step, wherein the first polymer coating layer conveys improved adhesion properties to the second polymer layer, which is supposed to be applied on the entire surface or respectively it is supposed to be a continuous layer.

Polymer A and polymer B can also be identical and advantageously they are different only as far as their concentration in the coating solution is concerned.

The present invention therefore relates to methods for completely coating the surfaces of lattice-like or mesh-like endoprostheses, in particular stents, wherein in a first coating step the struts forming the lattice-like or mesh-like structure of the endoprosthesis are covered completely or partially with a polymer coating and in a second coating step the entire surfaces of at least a part of the interstices between the struts forming the lattice-like or the mesh-like structure of the struts are coated with a polymer coating.

This means that at first the solid scaffolding of the endoprosthesis is provided with a polymer coating, wherein the coating encloses the individual struts. Preferably at least 50%, further preferred at least 70%, further preferred at least 80%, still further preferred at least 90% and in particular preferred at least 96% of the strut segments between two intersection points are provided with the first polymer coating. Moreover it is preferred that at least 50%, further preferred at least 70%, further preferred at least 80%, still further preferred at least 90% and in particular preferred at least 96% of the intersection points be covered with the first polymer coating. Points where at least two struts cross each other are referred to as intersection points.

The struts or respectively the intersection points are enclosed by the first coating like a tube or an insulation around a wire; nevertheless this coating only surrounds the individual struts and does not yet interconnect two adjacent struts. The first coating serves as a support layer for imparting improved adhesion properties to the superjacent coating which is supposed to extend over the interstices between the struts and the intersection points.

According to the invention it is preferred that the first coating be dried or respectively allowed to dry or respectively cured and subsequently wetted or soaked or partially dissolved or exposed to partial dissolution before the second coating is applied. The second coating extends over or respectively covers or respectively overcoats the interstices between the struts and the intersection points of the lattice scaffolding of the endoprosthesis at least partially. Partially means that at least 50%, further preferred at least 70%, further preferred at least 80%, still further preferred at least 90% and in particular preferred at least 96% of a continuous surface or of the entire surface of the interstices are coated. Evidently, the second polymer layer covering the interstices also covers the struts and intersection points, but it is not compulsory that the same also covers the inner and outer surfaces thereof. Due to the subjacent polymer coating layer which provides for the adhesion properties, it is sufficient if for example the second polymer layer covers only the outer or inner surface of the struts and intersection points, i.e. the surface of the endoprosthesis. Furthermore, it is preferred but not compulsory that the surface of the endoprosthesis be coated completely according to the invention and not only on a part of its surface. A partial coating for example is advantageous if an active agent has to be supplied to the vessel solely on one side or if the tumor exerts pressure on the vessel from one side only. The term "partial coating" therefore refers to the coating of a lower, upper, back, front, right or left portion of an endoprosthesis. Partial coating however can also refer to the fact that for example only 50% of the interstice surface area relative to the entire surface area of the endoprosthesis is covered.

Moreover, the individual struts or intersection points of the endoprosthesis may have recesses or cavities which, for example, could be filled with a pharmacological agent and be covered with the first polymer coating and the second coating. Such covering of such recesses and cavities is prior art and is to be considered as a preferred embodiment, but not as the principal aspect of the present invention.

The uncoated endoprosthesis or respectively the bare stent can be made of conventional materials such as medical stainless steel, titanium, chrome, vanadium, tungsten, molybdenum, gold, nitinol, magnesium, zinc, alloys of the aforementioned metals, or can be composed of ceramic materials or polymers. These materials are either self-expandable or balloon-expandable and biostable or biodegradable.

The method for completely coating the surface of lattice-like or mesh-like endoprosthesis according to the invention comprises the following steps:
a) providing a discontinuous, lattice-like or mesh-like endoprosthesis with interstices between the struts which form the lattice or mesh.
b) at least partially coating the struts, which form the lattice or mesh, with a polymer A,
c) wetting the surface of the endoprosthesis coated with the polymer A with an organic solvent,
d) coating the entire surfaces of at least a part of the interstices between the struts forming the lattice-like or mesh-like structure with a polymer coating of a polymer B.

The terms "lattice-like or mesh-like endoprosthesis with a discontinuous surface" refer to the fact that the endoprosthesis is not a solid tube or a cylinder. "At least partially" or "of at least a part" has already been defined above by means of the percentages, and the term "wetting" not only comprises wetting of the first polymer layer but also swelling, partially dissolving or exposing to partial dissolution of the first layer. The wetting step preferably is carried out by spraying the endoprosthesis with an organic solvent or organic solvent mixture or by immersing the endoprosthesis into an organic solvent or organic solvent mixture or by storing the endoprosthesis in an atmosphere saturated with an organic solvent or organic solvent mixture.

Another embodiment of the present invention is a method for coating the entire surfaces of lattice-like or mesh-like endoprostheses, said method comprising the following steps:
a) providing a discontinuous, lattice-like or mesh-like endoprosthesis comprising struts having an inner surface and an outer surface with interstices between the individual struts,
b) at least partially coating the inner and the outer surface of the struts with a polymer A,
c) wetting the surface of the endoprosthesis coated with the polymer A with an organic solvent,
d) coating the entire surfaces of at least one part of the inner and/or outer surface as well as the interstices between the struts with a polymer coating of a polymer B.

Assuming that the struts are approximately round, the term "inner surface" refers to the portion of the surface of the struts which is facing the longitudinal axis of the endoprosthesis and the term "outer surface" describes the portion not facing the inner surface. Therefore, only the terms inner and outer surface are clearly differentiated.

Preferably, the coating step b) is performed by means of spray coating or electrospinning, whereas the steps c) and d) are preferably performed by means of dip coating, micropippetting, electrospinning or/and the "soap bubble method".

The polymer surface can be coated completely or partially with a polymer C on the inner surface and/or on the outer surface.

Thus, it is important, for example for the luminal side of a tracheobronchial stent that it remains sufficiently slidable for not interfering with the evacuation of secretion, mucus, and the like. The hydrophilicity can be increased by coating with an appropriate polymer such as polyvinyl pyrrolidone (PVP).

The preferably uncoated endoprostheses used have a structure which disposes of recesses or interstices located between inner and outer surface rather than a continuous structure.

The reference made to the terms "inner and outer surfaces" shows that the endoprostheses used for the method according to the invention preferably dispose of a tubular structure. The endoprostheses to be coated are preferably elongated and hollow bodies such that tubular, spiral, cylindrical, mesh-like, braided and/or lattice-like structures are preferred.

This coating method overcomes the described shortcomings of the prior art with respect to complete surface coating and thus, eliminates the risks which the patient is exposed to.

Such medical devices which can be used according to the invention can be coated, on the one hand, by applying a coating on the solid material, for example the individual struts of a stent, and by filling the open area which is defined by the struts with a polymer layer B. This polymer layer is capable of covering the interstices of the stent struts coated with polymer A thanks to the polymer properties. The stability of the coat is a function of the two combined layers of polymer B and polymer A, which enclose the elements of the medical device.

Thus any medical device having such interstices in the surface structure can be coated in accordance with the invention, as is the case for example with stents showing such interstices between the individual struts.

Coating of the solid parts, for example of the individual struts of endoprosthesis, preferably is carried out by means of spray coating or electrospinning and the thus obtained layer is considerably thinner than the coating layer which is deposited on the entire surface. The first coating step can also be performed by means of a dipping method, plasma deposition method or gas phase coating.

Preferably, a polymer A is used in the first coating step whereas in the second coating step a polymer B is used, but it is also possible to use the same polymer in both coating steps.

A biodegradable or/and biostable polymer A for the first coating and of a biodegradable or reabsorbable polymer A or/and biostable polymer for the covering second coating depending on the type of application may be used.

The following polymers can be cited as biologically stable polymers or polymers with slow biodegradability: polyacrylic acid and polyacrylates such as polymethylmethacrylate, polybutylmethacrylate, polyacrylamide, polyacrylonitriles, polyamides, polyetheramides, polyethylene amine, polyimides, polycarbonates, polycarbourethanes, polyvinyl ketones, polyvinyl halides, polyvinylidene halides, polyvinyl ethers, polyvinylarenes, polyvinyl esters, polyvinyl pyrrollidones, polyoxymethylenes, polyethylene, polypropylene, polytetrafluoro-ethylene, polyurethanes, polyolefine elastomers, polyisobutylenes, EPDM gums, fluorosilicones, carboxymethyl chitosans, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulphones, polyethersulphones, epoxy resins, ABS resins, silicone prepolymers, silicones such as polysiloxanes, polyvinyl halogens and copolymers, cellulose ethers, cellulose triacetates, chitosan, chitosan derivatives, polymerizable oils such as linseed oil and copolymers and/or mixtures thereof.

Furthermore, in a step prior to the step of coating with polymer A, a hemocompatible layer preferably can be bound covalently to the uncoated surface of the medical device or can be immobilized on the same by means of crosslinking, for example with glutardialdehyde. Such layer which does not activate the blood coagulation is useful when uncoated stent material comes in contact with blood. Thus, it is preferred firstly to provide a partially coated stent, such as for example described in U.S. Pat. No. 595,159 for the treatment of aneurysms, with such hemocompatible layer.

The preferable hemocompatible layer is made of the following preferred agents: naturally obtained heparin as well as regioselectively prepared derivatives thereof with different degrees of sulphation and acetylation in the molecular weight range of the pentasaccharide, which is responsible for the antithrombotic effect thereof, to the standard molecular weight of the commercially available heparin of about 13 kD; heparan sulphates and derivatives thereof, oligosaccharides and polysaccharides of the erythrocyte glycocalix, oligosaccharides, polysaccharides, completely desulphated and N-reacetylated heparin, desulphated and N-reacetylated heparin, N-carboxymethylated and/or partially N-acetylated chitosan, polyacrylic acid, polyether ether ketones, polyvinyl pyrrolidone and/or polyethylene glycol as well as mixtures of these substances.

As biodegradable or absorbable polymers for example the following polymers can be used: polyvalerolactones, poly-ϵ-decalactones, polylactides, polyglycolides, copolymers of the polylactides and polyglycolides, poly-ϵ-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-ones), poly-paradioxanones, polyanhydrides such as polymaleic anhydrides, polyhydroxymethacrylates, fibrin, polycyanoacrylates, polycaprolactone dimethylacrylates, poly-β-maleic acid, polycaprolactonebutyl-acrylates, multiblock polymers such as from oligocaprolactonedioles and oligodioxanonedioles, polyetherester multiblock polymers such as PEG and poly(butyleneterephthalate), polypivotolactones, polyglycolic acid trimethyl-carbonates, polycaprolactone-glycolides, poly(γ-ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethyl carbonates, polyiminocarbonates, poly(N-vinyl)-pyrrolidone, polyvinylalcohols, polyesteramides, glycolated polyesters, polyphosphoesters, polyphosphazenes, poly[p-carboxyphenoxy)propane], polyhydroxypentanoic acid, polyanhydrides, polyethylene oxide-propylene oxide, soft polyurethanes, polyurethanes with amino acid residues in the backbone, polyetheresters such as polyethylene oxide, polyalkeneoxalates, polyorthoesters as well as their copolymers, carrageenanes, fibrinogen, starch, collagen, protein based polymers, polyamino acids, synthetic polyamino acids, zein, modified zein, polyhydroxyalkanoates, pectic acid, actinic acid, modified and unmodified fibrin and casein, carboxymethyl sulphate, albumin, moreover hyaluronic acid, heparan sulphate, heparin, chondroitine sulphate, dextran, β-cyclodextrines, and copolymers with PEG and polypropyleneglycol, gummi arabicum, guar, gelatine, collagen, collagen-N-Hydroxysuccinimide, modifications and copolymers and/or mixtures of the substances mentioned above.

Furthermore, it is preferred that the outer surface resulting from the second step of completely coating the surface be not even or plane but that the structure of a stent i.e. the structure of the struts, be still visible. The advantage thereof consists in the fact that the outer coated surface of the endoprosthesis facing the vessel wall has a corrugated and rough structure, which assures an improved fixation within the vessel.

Furthermore it is preferred that the second coating step consist of two stages. The medical devices to be coated are preferably tubular with at least one open end on one side, mostly even on both sides. For performing the second coating step [steps c), d)], said medical device is preferably placed on a rod or a pin having the desired diameter and is immersed into an appropriate solvent. The rod or pin has a diameter corresponding to the desired future inner diameter of the medical device after the coating.

It is further preferred that the medical device be coated by means of dip coating such that the layer forms a smooth, uniform coating on the inner surface of the medical device although deposited on the outer surface in a manner that causes the surface structure of the medical device to be raised from the coating or respectively to be maintained as a structure visible below the coating. For this purpose, the first coating step is necessary, since a distance, which corresponds to the polymer layer between stent struts and the rod and which is requisited for dip coating of the entire surface, can be generated only due to the coating with polymer A. The polymer solution B can now flow into these intermediate areas open on the luminal side of the medical device and fill the same.

Preferably organic solvents with appropriate wetting characteristics for suitable dissolution of polymer B are used as solvents. The used solvent may contain polymer B already in a low concentration, such that the viscosity of the solution is low enough for still providing for proper and complete wetting of, in particular, the inner surfaces of the medical device. The concentration of the polymer B in the solvent used for wetting according to step c) is lower than the concentration of the polymer B in the solution used for coating according to step d). Solvents having a low vapor pressure, such as acetone, THF, methylene chloride, chloroform, carbon tetrachloride, methanol, ethanol, ether, petroleum ether, hexane, heptane, cyclohexane, benzene, toluene, ethyl acetate or acetic acid are used as solvents.

The wetting step c) has the advantage of preventing the inclusion of air bubbles in the polymer layer of polymer B covering the entire surface and a strong adhesion or respectively fusion between the polymer layer of polymer A and the polymer layer of polymer B, since both polymers are soluble either completely (A and B) or partially (A) in the used solvent.

In lieu of the wetting step or in addition to the same, the two polymer layers can be fused upon exposure to heat.

The surface of the medical device wetted with solvent or already wetted with a diluted solution of the polymer B or partially coated is subsequently being completely coated with a more concentrated solution of the polymer B. Said coating may be carried out by placing the medical device in a more concentrated dipping solution B or by enhancing the concentration the diluted solution of the polymer B, wherein the first embodiment will be preferred.

Furthermore, it is preferred that the wetting solution and the coating solution contain the same solvent, however, this fact is not compulsory. Nevertheless, it is important that the solvent for the wetting solution and the solvent for completely coating the surface according to step d) can be mixed and preferably have the same ability to dissolve polymer B or do not lead to precipitation of the polymer B or to the clouding of the coating solution.

As a special case of the dipping method, interfacial polycondensation can be used for coating the entire surfaces of the medical device. In this method, the dipping solution consists of two monomer solutions which cannot be mixed, wherein the polymer which is not soluble in both monomer solutions forms a thin film on the phase interface. The film is formed uniformly on the edge of the reaction vessel by slowly and carefully withdrawing said film as a fiber from the center of the reaction vessel. Said process is carried out until the monomer solutions are diluted to an extent that causes the tube to be disrupted.

Upon introduction of the stent into the lower solution, the same can lift the polymer film, provided that the lifting speed is appropriate, such that the polymer film encloses the body to be coated like a tube.

This method is perfectly suitable for forming the polymer coating supposed to provide a coating layer which covers the entire surface and which is made of e.g. an acid chloride or diamines or diols. The reaction vessel is a U-shaped tube. The acid chloride is preferably dissolved in an organic solvent having a density greater than 1 g/ml. As organic solvents or mixtures of organic solvents methylene chloride, chloroform or carbon tetrachloride can be used. A pharmacological agent can for example be added to the organic solution containing the acid chloride, as far as said pharmacological agent does not react with the acid chloride. The diamine (or e.g. diol) is being solved in water. It is possible to add a hydrophilic pharmacological agent to the aqueous solution, as long as said agent does not react with the diamine or respectively with the diol. The organic solution of the acid chloride, which possibly contains a lipophilic pharmacological agent, is filled into the U-shaped reaction vessel, and only one leg of the reaction vessel is filled with the aqueous solution of the diamine which possibly contains a hydrophilic pharmacological agent, such that the interfacial polymerization takes places exclusively in this leg and terminates after the formation of an interfacial film. The endoprostheses provided with the first coating are placed on a mandrel and are immersed into the leg of the reaction vessel containing only the organic solution of the acid dichloride along a guiding wire and pass through the bottom of the reaction vessel. The delay of movement is sufficient for soaking or exposing to partial dissolution or partially solving the already present polymer coating which encloses the individual struts. The endoprostheses are withdrawn in the second leg of the reaction vessel where the polymer interfacial film has formed and the organic solution is overcoated with the aqueous solution of the diamine. Upon passivation of the interface, the film adheres to the endoprosthesis and is drawn out along with the endoprosthesis, wherein the film takes the shape of a tube and encloses the endoprosthesis like a coat.

In a preferred embodiment, the refilling of the organic solution as well as of the supernatant aqueous solution is performed in a computer-controlled manner and the endoprostheses are transported through the reaction apparatus one after the other like on a conveyor belt such that the polymer interfacial film is not torn or interrupted and is deposited like a tube around a plurality of consecutively arranged endoprostheses. Cutting of the polymer tube, folding or respectively turning over its edges around the ends of the endoprosthesis for reinforcing the same as well as possibly further curing the polymer coating layer which completely covers the surface is performed according to known standard procedures depending on the requirements and the polymer.

Coating the entire surfaces of a medical device or of a part of a medical device according to step d) can also be performed by means of micropippetting into the individual interstices. Here, the selected areas of the medical device are filled with the micropipette such that the polymer film uniformly covers the space between the limiting elements of the medical device.

The coating in step d) can also be designed by means of the so-called electrospinning, wherein the variation of the reaction parameters offers the possibility of producing individual polymer fibers ranging from diameters in the nanoscale to layers completely covering the surface, as well as the possibility of applying the same on an object in a directed manner. This method offers the possibility of designing the spaces also as structural elements if necessary, such as for example required for tissue engineering applications.

A further variation for coating the entire surfaces of such implants consists in "inflating" solutions of appropriate elastomers like a balloon via a ring by means of nitrogen or oxygen or another appropriate gas, in analogy to the formation of soap bubbles. The endoprosthesis can easily be introduced into this balloon by means of a pin which is placed exactly in the center of the ring diameter during the formation of the bubbles.

If the hollow body is inserted into such a "balloon" formed from the polymer solution before the same diminishes in size due to the shrinking perimeter, the polymer film will enclose the hollow body, and the struts are thus visible as protrusions. In a second step the body coated on the outer surface is coated on the inner surface so that on the one hand, a smooth surface is formed and one the other hand, the polymer on the outer surface is fused to the inner polymer, both polymers thus forming a unit. This can be achieved for example by placing the coated stent on a mold, the diameter of which is slightly smaller than that of the coated endoprosthesis and by filling the interstice with a solution of the polymer. Subsequently, the hollow body thus coated on the inner surface is removed carefully from the tool and dried. The interfacial tension and the cohesive forces of a polymer solution can be used as well for partial coating by applying the polymer film to individual segments.

The solution for the first coating preferably contains a concentration of polymer A of 0.01 to 80% per weight, preferably of 0.1 to 50% per weight, in particular preferred of 0.5 to 25% per weight.

The thickness of this first subjacent layer, which is preferably applied by spray coating or electrospinning, is preferably between 0.0001 and 1000 µm, further preferred between 0.001 and 500 µm and in particular preferred between 0.1 and 250 µm.

The concentration of polymer B for completely coating the surface is preferably between 0.1 and 80% per weight, further preferred between 1 and 50% per weight and in particular preferred between 5 and 30% per weight.

The thickness of the second polymer layer made from polymer B or C, which optionally contains one or more pharmacological agents is preferably between 0.1 and 1500 µm, further preferred between 1 and 1000 µm and in particular preferred between 2 and 500 µm.

Furthermore it is preferred that the outer layer of the inner surface of the medical device or respectively the endoprosthesis be made of a polymer B' which is different from that of the outer surface, which is for example coated with the polymer B". Such coatings can be obtained for example by placing the medical device or respectively the endoprosthesis on a pin or rod, the diameter of which is smaller than the medical device or respectively the endoprosthesis as such, and by subsequently coating the inner as well as the outer surface of the medical device or respectively the endoprosthesis with the polymer B', this step being followed by a further coating step, wherein only the outer surface can be coated with the polymer B", since the interstice between the inner surface of the medical device or respectively the endoprosthesis and the surface of the pin or rod already is filled completely with the polymer B'. Another possibility consists in the use of a pin or rod of the same diameter as the medical device or respectively the endoprosthesis, and in coating the outer surface as well as the interstices with a polymer B', followed by subsequent application of a further coating on the inner surface of the medical device or respectively the endoprosthesis which serves for applying the polymer B'''.

The application of the first subjacent and thin coating layer is in particular advantageous for the application of medical devices or respectively endoprosthesis made of metal, metal salts, metal alloys or mixtures of the above mentioned materials for offering protection against ion exit, corrosion as well as formation of galvanic couples. Said subjacent coating layer can be omitted if medical devices or respectively endoprosthesis made of non-metallic materials such as for example plastic materials (for example teflon) are used. In such a case, the coating layer covering the entire surface can be bound to the material of the medical device.

In further preferred embodiments, solutions of the polymer A and/or of the polymer B are used, which further contain at least one antiproliferative, anti-migration, antiangiogenic, anti-inflammatory, antiphlogistic, cytostatic, cytotoxic and/or antithrombotic active agent. This active agent can be covalently bound, adhesively bound or ionically bound. Thus, coated medical devices or respectively endoprostheses which contain at least one active agent in the layer with polymer A and/or preferably at least one active agent in the layer with polymer B, preferably in the form of a layer releasing an active agent (drug release system) are obtained. Evidently it is also possible to apply the active agent(s) on the first and preferably the second layer in an additional coating step, so that an additional active agent layer is present.

The concentrations per active agent are preferably in the range of 0.001-500 mg per cm² of the entire coated surfaces of the endoprosthesis, i.e. the surface is calculated taking into consideration the total surface of the coated struts and the surface of the covered interstices between the struts.

The active agent(s) can be present beneath, in and/or on the first and/or second polymer layer depending on the coating method. Preferably, the following active agents can preferably be used as antiproliferative, anti-migration, anti-angiogenic, anti-inflammatory, antiphlogistic, cytostatic, cytotoxic and/or antithrombotic active agents: sirolimus (rapamycin), everolimus, pimecrolimus, somatostatin, tacrolimus, roxithromycin, daunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-ydroxyoxycyclophosphamide, estramustine, melphalan, ifosfamide, trofosfamide, chlorambucil, bendamustine, dacarbazine, busulfan, procarbazin, treosulfan, temozolomide, thiotepa, daunorubicin, Doxorubicin, aclarubicin, epirubicin, mitoxantrone, idarubicin, bleomycin, mitomycin, dactinomycin, methotrexate, fludarabine, fludarabin-5'-dihydrogenphosphat, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharanthin, 8-α-ergoline, dimethyl ergoline, agroclavin, 1-allyl lisuride, 1-allyl terguride, bromerguride, bromocriptine (2-bromo-12'-hydroxy-2'-(1-methylethyl)-(2-methylpropyl)-5'-α-ergotaman-3',6',18-triones,) elymoclavine, ergostristine (12'-hydroxy-2'-(1-methylethyl)-5'-(phenylmethyl)-(5'-α)-ergotaman-3',6',18-triones), ergocristinine, ergocornine (12'-hydroxy-2',5'-bis(1-methylethyl)-(5'-α)-ergotaman-3',6',18-triones), ergocorninine, ergocrypine (9Cl-12'-hydroxy-2'-(1-methylethyl)-5'-(2-methylpropyl)-(5'-α)-ergotaman-3',6,18-triones), ergometrin, ergonovine, (ergobasine, INN: ergometrine, 8,β(S)-9,10-didehydro-N-(2-hydroxy-1-methylethyl)-6-methyl-ergoline-8-carboxamid), ergosine, ergosinine, ergometrinine, ergotamine (9Cl-12'-hydroxy-2'methyl-5'-(phenylmethyl)-(5'-α)-ergotaman-3',6', 18-triones). ergotaminine, ergovaline (12'-hydroxy-2'-methyl-5'-(1-methylethyl)-(5-α)-ergotaman-3',6',18-triones), lergotrile, lisuride (CAS no: 18016-80-3,3-(9,10-didehydro-6-methylergoline-8-α-yl)-1,1-diethylurea), lysergol, lysergic acid (D-lysergic acid), lysergic acid amide (LSA, D-lysergic acid amide), lysergic acid diethylamide (LSD, D-lysergic acid diethyl amide, INN: lysergic amide, 8,β-9,10-Didehydro-N,N-diethyl-6-methyl-ergoline-8-carboxamide), isolysergic acid (D-isolysergic acid), isolysergic amide (D-isolysergic amide), isolysergic acid diethylamide (D-isolysergic acid diethyl amide), mesulergine, metergoline, methergine (INN: methylergometrine, 8,β(S)-9,10-Didehydro-N-(1-(hydroxymethyl)propyl)-6-methyl-ergoline-8-carboxamide), methylergometrine, methysergide (INN: methysergide, 8,β-9,10-didehydro-N-(1-(hydroxymethyl)propyl)-1,6-dimethyl-ergoline-8-carboxamide), pergolide (8,β-8-(methylthio)methyl)-6-propyl-ergoline), proterguride and terguride, celecoxib, thalidomide, Fasudil®, cyclosporine, SMC-proliferation-inhibitor-2ω, epothilones A and B, mitoxanthrone, azathioprine, mycophenolate mofetil, c-myc antisense, b-myc antisense, betulinic acid, camptothecin, PI-88 (sulphated oligosaccharide), Melanocyte-stimulating hormone (α-MSH), activated protein C, IL1-β-inhibitor, thymosin α-1, fumaric acid and its esters, calcipotriol, tacalcitol, lapachol, β-lapachone, podophyllotoxin, betulin, 2-ethylhydrazide of podophyllic acid, molgramostim (rhuGM-CSF), peginterferon α-2b, lanograstim (r-HuG-CSF), filgrastim, macrogol, dacarbazine, basiliximab, daclizumab, selectin (cytokine antagonist), CETP inhibitor, cadherins, cytokine inhibitors, COX-2-inhibitor, NFkB, angiopeptin, ciprofloxacin, fluroblastin, monoclonal antibodies which inhibit the muscle cell proliferation, bFGF antagonists, probucol, prostaglandins, 1,11-Dimethoxycanthin-6-one, 1-Hydroxy-11-Methoxycanthin-6-one, scopoletin, colchicine, NO donors such as pentaerythritol tetranitrate and sydnonimines, S-nitroso derivatives, tamoxifen, staurosporine, β-estradiol, α-Estradiol, estriol, estrone, ethinyl estradiol, fosfestrol, medroxyprogesterone, estradiol cypionates, estradiol benzoates, tranilast, kamebaukarin and other terpenoids which are applied in the therapy of cancer, verapamil, tyrosine kinase inhibitors (tyrphostines), cyclosporine A, paclitaxel and derivatives thereof such as 6-α-hydroxy-paclitaxel, baccatine, taxoteres, macrocyclic oligomers of carbon suboxide (MCS) obtained synthetically and from native sources and derivatives thereof, mofebutazone, acemetacin, diclofenac, lonazolac, dapsone, o-carbamoyl-phenoxy-acetic acid, lidocaine, ketoprofen, mefenamic acid, piroxicam, meloxicam, chloroquine phosphate, penicillamine, tumstatin, avastin, D-24851, SC-58125, hydroxychloroquine, auranofin, sodium aurothiomalate, oxaceprol, β-sitosterin, ademetionine, myrtecaine, polidocanol, nonivamide, levomenthol, benzocaine, aescin, ellipticine, D-24851 (Calbiochem), colcemid, cytochalasin A-E, indanocine, nocadazoles, S 100 protein, bacitracin, vitronectin receptor antagonists, azelastine, guanidyl cyclase stimulator, tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefoxitin, tobramycin, gentamycin, penicillins such as dicloxacillin, oxacillin, sulfonamides, metronidazole, antithrombotics such as argatroban, aspirin, Abciximab, synthetic antithrombin, bivalirudin, coumadin, enoxoparin, desulphated and N-reacetylated heparin, tissue plasminogen activator, GpIIb/IIIa platelet membrane receptor, factor $X_a$ inhibitor antibody, interleukin inhibitors, heparin, hirudin, r-hirudin, PPACK, protamine, sodium salt of 2-methylthiazolidine-2,4-dicarboxylic acid, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thioprotease inhibitors, prostacyclin, vapiprost, interferon α,β and γ, histamine antagonists, serotonin blockers, apoptosis inhibitors, apoptosis regulators such as p65, NF-kB or Bcl-xL, antisense oligonucleotides, halofuginone, nifedipine, Tocopherol, vitamin B1, B2, B6 and B12, folic acid, molsidomine, tea polyphenols, epicatechin gallate, epigallocatechin gallate, Boswellic acids and derivatives thereof, leflunomide, anakinra, etanercept, sulfasalazine, dicloxacillin, tetracycline, triamcinolone, mutamycin, procainimide, D24851, SC-58125, retinoic acid, quinidine, disopyrimide, flecainide, propafenone, sotalol, amidarone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprotozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanols A, B and C bruceantinoside C, yadanziosides N and P, isodeoxyelephantopin, tomenphantopin A and B, coronarin A,B,C und D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, moreover cymarin, apocymarin, aristolochic acid, anopterin, hydroxyanopterin, anemonin, protoanemonin, berberina, cheliburin chloride, cicutoxin, sinococuline, combrestatin A and B, cudraisoflavone A, curcumin, dihydronitidine, nitidine chloride, 12-β-hydroxypregnadiene-3,20-dione, bilobol, ginkgol, ginkgolic acid, helenalin, indicine, indicine-N-oxide, lasiocarpine, glycoside 1α, justicidin A and B, larreatin, malloterin, mallotochromanol, isobutyrylmallotochromanol, maquiroside A, marchantin A, maytansine, lycoridicine, margetine, pancratistatin, liriodenine, oxoushinsunine, aristolactam-AII, bisparthenolidine, periplocoside A, ursolic acid, deoxypsorospermin, psycorubin, ricin A, sanguinarine, manwu wheat acid, methylsorbifolin, chromones from spathelia, stizophyllin, akagerine, dihydrousambaraensine, hydroxyusambarine, strychnopentamine, strychnophylline, usambarine, usambarensine, berberine, daphnoretin, laricir-esinol, methoxylariciresinol, syringaresinol, umbelliferone, afromoson, acetylvismione B, desacetylvismione A, vismione A and B and sulphurous amino acids such as cystine as well as hydrates, solvates, enantiomers, racemates, enantiomer mixtures, diastereomeric mixtures and mixtures of the active agents mentioned above.

The methods according to the invention are adapted for coating for example endoprostheses and in particular stents such as for example coronary stents, vascular stents, tracheal stents, bronchial stents, urethral stents, esophageal stents, biliary stents, renal stents, stents for use in the small intestine, stents for use in the large intestine. Moreover, guiding wires, helices, cathethers, canulas, tubes as well as generally tubular implants or parts of the above mentioned medical devices can be coated according to the invention provided that a structural element comparable to a stent is contained in such medical device. As far as expandable medical devices or respectively endoprostheses are used, the coating preferably is carried out during the expanded state of the respective device.

The coated medical devices are preferably used for maintaining patency of any tubular structure, for example the urinary tract, esophaguses, tracheae, the biliary tract, the renal tract, blood vessels in the whole body including brain, duodenum, pilorus, the small and the large intestine, but also for maintaining the patency of artificial openings such as used for the colon or the trachea.

Thus, the coated medical devices are useful for preventing, reducing or treating stenoses, restenoses, arterioscleroses, atheroscleroses and any other type of vessel occlusion or vessel obstruction of lumens or openings.

Furthermore it is preferred that the length of the coating layer which contains polymer B and which covers the entire surface exceeds that of the endoprosthesis so that the ends of the endoprosthesis do not correspond to the end of the coating layer. The overlapping part of the shell is placed around the edges of the endoprosthesis on the outer surface and the thus formed edges are being integrated into the subjacent polymer layer B under pressure and increased temperature. Thus, a continuous coating of the edges of the endoprosthesis is assured, which eliminates at the same time the danger of detachment on these weak points. Moreover, a handling element can be mounted below the edge by means of which the stent can be removed safely at any time. Thus, a polymer fiber can be disposed circumferentially in the folding, wherein the fiber projects through the polymer layer from the edge to the outer surface in the form of a loop on one or two opposite sides.

Another possibility consists in the use of this marginal region as a reservoir for active agents or respectively for introducing active agents especially into this marginal region, wherein these active agents can be different from those possibly present in/on the completely coated surface of the hollow body.

Summarizing, it can be stated that a method for coating endoprosthesis and in particular stents, but also other biostable as well as biodegradable stent-like medical device was surprisingly found, which method overcomes the described disadvantages of the prior art. The particularly problematic risk of detachment of the shell, the difficulty of providing a secure fixation within the vessel, the danger of penetration of the layer at the edges and the contact between metal and vessel wall, which causes the tissue irritation, can be avoided thanks to the method according to the invention. Therein, the shell enclosing the stent is provided with the flexibility of the stent, but also contributes in imparting mechanical stiffness to the medical device. Additionally, there exists the possibility of introducing active agents in a side-specific manner, such as a cytostatic which can diffuse into the vessel wall, and for example an antibiotic which prevents infections on the inner surface of the medical device. Moreover, further optimizations concerning the adaptation to the physiological conditions at the respective implantation site can be achieved thanks to the possibility of applying different coatings on the inner and outer surface.

Further additives are possible, e.g. substances such as barium sulphate or precious metals, which allow for imaging an implanted, thus coated medical device in radiograms. Furthermore, the outer surface and the inner surface can be enclosed with different materials, such as described above. Thus, for example, a medical device which possesses a hydrophobic polymer shell on the outer surface whereas the inner surface is made of hydrophilic polymer can be produced.

This method offers a variety of possibilities for applying any biostable or biodegradable coating materials containing or not containing additives on medical devices, if necessary in the form of a shell.

The problem of a possibly occurring detachment from the medical product is eliminated in that the inner surface of the stent is not being coated completely as described in WO 2005/030086, but in hat the polymer skin is being applied on the outer surface. Although the coating is applied on the outer surface, the stent inner surface can be covered by a smooth and continuous polymer layer if necessary, whereas the coated outer surface also has a continuous coating layer not showing any gaps. The rough areas of the surface structure, in the case of the stent formed by the stent struts, remain as uneven areas below the coating layer and are raised from the same, but do not cause any gaps in the coating layer. Thus, despite the fact that the covering is applied on both sides as well as on the entire surface, secure fixation within the vessel is ensured.

By means of the described method, it is achieved that on the one hand the detachment of the coating is no longer possible, since the coating forms a unit with the implant, and on the other hand, the fixation of the coated stent is ensured even under the most extreme conditions. Tissue irritations cannot be caused since the metal does not contact the tissue.

Any implant irrespective of its shape and material can thus be provided completely or incompletely with a continuous cover.

It is important that the cover be an integrated part of the implant, so that, thanks to this method, under no circumstances separation between polymer layer and stent or respectively a detachment of the polymer layer from the stent takes place. At the same time, the coating can add to the mechanical stiffness of an implant without affecting the flexibility thereof.

The method according to the invention for coating the entire surfaces preferably consists of three separate process steps.

In the first step, only the compounds of the implant and not the interstices are coated with a uniform and thin layer of a solution containing the selected polymer A. This coating step is important for the next coating step, which is supposed to cover the entire surface.

The polymer can be synthetically or naturally obtained or it can also be composed of mixtures of different biodegradable and/or biostable polymers. One or more active agents appropriate for promoting the healing process due to a time-controlled release can be admixed. Appropriate active agents can be selected depending on the disease, e.g. anti-inflammatory active agents, cytostatics and cytotoxics, antibiotics, anti-thrombotics, antimycotics, fungicides as well as the active agents mentioned above.

The second step, in which the surface of the implant coated with polymer A or the implant segment is completely coated, is performed as an dipping process, by electrospinning or micropippetting.

For this purpose, the implant or respectively medical device is arranged on a mold which is adapted in size and shape, in analogy to a finger stall on a finger, but in a manner which prevents it from being displaced. Also, it must not be attached so tightly that it is deformed. The choice of the material the evidently stainless coating tool is made of is important, since the material properties of the tool affect for example the evaporation of the solvent from the solution.

If the micropippetting process and electrospinning methods are applied, the possibility of covering interstices of non adjacent segments of the medical device with polymer B exists, unlike in the dipping method.

In addition to the already described generation of smooth surfaces, electrospinning also enables to structure the inner or/and outer surfaces such that they form small-meshed or coarse-meshed networks in the interstices of the implant or respectively segment.

The coating process with polymer B itself preferably consists of two steps. The implant mounted on the tool or the segment of the implant to be coated is initially wetted with the pure solvent or respectively with a highly diluted solution of the polymer which is provided as a coating. For said purpose, dip coating is preferred. The present polymer coating A serves as a corrosion barrier between the metallic implant and a metallic covering tool.

On the one hand, the air bubbles formed upon dipping a body into a liquid can be removed; on the other hand, adhesion of the actual viscous coating solution thus is increased by partial dissolution of polymer A.

The distance between the implant and the tool obtained by coating with polymer A is essential for the second coating step, since only due to the existence of said distance the covering solution containing polymer B reaches the inner surface of the implant by means of the capillary effect and extends the surface of the coating tool into the free interspaces of the adjacent implant elements completely coated with polymer A.

The implant thus obtains the required smooth, even surface on its inner surface. On the outer surface, the elements of the implant are raised from the polymer layer, which provides for secure fixation of the implant also under the extreme conditions which can for example be present in the esophagus or the trachea.

Moreover, it is thanks to this method that it is possible to provide the outer surface with a polymer material which is different to that of the inner surface. Thus, the inner surface can additionally be covered with a hydrophilic polymer e.g. in the case of the trachea stent. This can improve the drainage of mucus even more.

Besides, the additional possibility of introducing appropriate active agents into the coating exists, wherein the active agents on the outer surface can be different from those incorporated in the inner surface.

For avoiding that injuries are caused by the ends of the implant, a further step is advantageous for such medical devices the surfaces of which have to be completely coated on said ends. The obtained coating is not cut off along the edge of the implant, but a protruding part is left on both ends, and said protruding part is folded over the edge of the implant during this last working step. The folded-over portion is integrated into the subjacent layer by application of pressure and heat. The cutting edge is no longer visible. The folded edge and the subjacent coating are combined in such a way that it is no longer possible to distinguish one from the other. Only thanks to this the risk that the coating might detach on the edge is eliminated. Another advantage consists in the fact that that the thicker coating cannot be easily damaged. This can happen any time for example if a trachea stent is being displaced during the process of coughing such that strut ends can penetrate through the thinner coating. As a consequence, injuries in the trachea are caused due to the then uncoated, open end tip, but the same also represent a weak point within the coating, which could entail further problems. In addition to the thus achieved increased safety, the thicker marginal layer also allows for the attachment of elements such as for example necessary for removing the implant, wherein said layer can be circumferentially disposed about the edge and thus be sealed to the device. Active agents can as well be introduced into the edge of this folded coating and subsequently slowly be released from said reservoir.

There is also the possibility of improving the visibility in radiographic processes, for example by means of heavy metal salts or precious metals which can be incorporated into the thicker edges as well as into the entire coating without the risk of galvanic couples being formed, which couples can be easily generated in the case of a direct contact between the metals.

Thus, it has been shown that the methods described herein fully overcome the problems of known endoluminal prostheses described herein. For this purpose, variation possibilities concerning the shape and material of the implant, of the biocompatible coating material as well as the active agents are unlimited and first of all result from combinations useful for the patient.

Thus, up to now, e.g. the use of stents for the restriction of biliary tract carcinomas is not a standard procedure. However, in only 10% of the cases, a surgical removal is successful. Medium life expectancy of such patients is of 1 year. The use of an implant completely coated according to this method and adapted to application in the biliary tract, which could optionally contain a chemotherapeutic agent, could on the one hand prevent the constriction of the body lumen in that the endoprosthesis exerts a certain counter pressure and at the same time, could slow down or even stop tumor growth and thus would at least provide a life prolonging treatment while maintaining high or good quality of life.

Furthermore, the coating according to the invention can also be used in the vascular system. In the case of the formation of aneurysms it can be used for example in a manner that prevents an increase of the aneurysm due to the continued supply with blood.

As an additional example such medical device can serve as a base for tissue engineering, wherein electrospinning seems to be the principal method of choice.

EXAMPLES

Example 1

Precoating of Stents by Means of a Spraying Process

A stent is fixed on the rod of a rotator and is sprayed with 1% polyurethane solution at very slow rotational speed by slowly moving the pistol upwards and downwards. After being sprayed, the stent is of a mat gray color, such that an optical spray control can be conducted. It is particularly important that the edge is sprayed accurately which can be ensured by additional circumferential spraying. Subsequently, the stent is allowed to dry.

Example 2

Polysulphone Spray Solution 176 mg of PS (polyether sulphone, Odel®, available from Solvay are weighed out and topped up to 20 g with chloroform (0.88% PS solution) and are sprayed onto the stent as in example 1.

Example 3

Coating the Entire Surfaces of a Sprayed Stent by Dip Coating

Polyurethane is dissolved in THF, so that a 14% solution is obtained. A stent precoated according to example 1 is carefully mounted on the adequate mold. The tool with the stent mounted thereon is immersed head first into pure THF until rising air bubbles can be seen. Subsequently, the stent is slowly immersed into the 14% polyurethane solution. After 15 seconds, the core is slowly removed and immediately oriented horizontally and the core is turned so that the PU is uniformly distributed on the stent and allowed to dry.

Once the PU has stopped running, the core is allowed to dry under the fume hood and subsequently tempered at 95° C. during 45 min in the drying oven. After cooling it is dipped into a warm 0.3% SDS solution for detaching the stent from the tool. After purification under running water and rinsing with 0.5 m NaOH, it is thoroughly rinsed under running water and in DI water.

Example 4

Coating of the Entire Surfaces of a Sprayed Stent with PU/Terguride by Dip Coating The dipping solution consists of 30% per weight of terguride in polymer, which subsequently is diluted to 10% with THF. The subsequent procedure is as described in example 2.

Example 5

Coating of the Entire Surfaces of a Sprayed Stent with PU/Cyclosporine by Dip Coating The dipping solution consists of 30% per weight of cyclosporine A in polymer, which subsequently is diluted to a concentration of 10% with THF. The subsequent procedure is as described in example 2.

Example 6

Coating of the Entire Surfaces of a Stent Coated with Paclitaxel According to a Spray Coating Method The stents the entire surfaces of which are coated with a polymer according to example 1 and example 2 are horizontally attached to a thin metal bar, which is mounted on the rotational axis of the rotation and feed device and which rotates at 10 rpm. The stents are mounted such that the inner surfaces of the stents do not come in contact with the bar. The stent is sprayed with the respective spraying solution at a feeding amplitude of 2.2 cm, a feed rate of 4 cm/s and a distance between stent and nozzle of 8 cm. After drying at room temperature (about 15 minutes) and subsequently in the fume hood over night, the stent is weighed again.

Preparation of the spraying solution: 44 mg of taxol are dissolved in 6 g of chloroform.

Example 7

Fold-Over of the Edge of the PU-Covered Stent

The protruding edge of the polymer shell is cleaned with ethanol in order to prevent that the PU sticks together. Subsequently, the PU edge is circumferentially folded over the edge of the stent. The edge is flattened until no more creases are visible. During this process, it is important that the edge be not folded over too tightly (no crown structure!), since otherwise the stent end could penetrate the covering and holes would be generated.

Example 8

Use of the Edge as a Reservoir for Active Agents

The overlapping edge of the polymer shell on both ends of the completely coated stent is folded back as described in example 6 and is filled prior to being flattened with 200 µl of a solution of 30% per weight of fasudil in ethanol/water (50:50 v:v) and subsequently slightly dried until the process can be continued as in example 6.

Example 9

Mounting a Handling Element for Removing the Stent

For this purpose, a tenacious polyurethane fiber is circumferentially mounted about the overlapping polymer edge of the hollow body coated according to example 3, such that the beginning and end of the fiber meet along a straight line and terminate directly below the stent end after the fold-over, as described in example 7. For forming the loop, the fiber is guided through the projecting polymer shell with a needle at an angle of 90° C. from the beginning of the fiber and brought back to the outer surface in a sufficient distance from the first puncture, such that a handle having an angle of 90° relative to the longitudinal axis of the stent and being oriented towards the center of the circle is formed. The same procedure is carried out at an angle of 270° from the beginning of the fiber before the end of the fiber reaches the beginning of the fiber. The subsequent fold-over of the edge changes the position of the two loops from the position which is perpendicular to the longitudinal axis into a position parallel to the same, such that the polymer loops on both sites can be considered as a loop-shaped extension of the coated hollow body. By means of sealing the folded edge as described in example 10, the PU fiber can be firmly integrated into the edge.

Example 10

Sealing of the Fold-Over

The folded edge is sealed by application of pressure and heat. For this purpose, the stent is placed on the mold again. Respectively one hose clamp padded with silicone foam strips is placed on each stent end and tightened by means of a torque wrench. Subsequently, the stents are placed in the drying oven at 95° C. for at least 4 hours. After cooling, the clamps are released and the stent is detached, purified and air-dried by wetting in SDS bath as in example 3.

Example 11

Hydrophilic Coating of the Luminal Side of a Completely Coated

The solvents isopropanol, methyl ethyl ketone and diacetone alcohol are mixed at a volume ratio of 1:2:1 and stirred in PVP to obtain a 35% solution.

The stent, having its entire surface coated with polymer, is mounted on a metal cone such that the PVP solution can be filled in the space between cone and stent. In doing so, it is important that no solution drips runs down the upper edge, as only the inner side is to be coated. After a short delay, the stent is lifted and the solution is allowed to drain off over the cone. The solution thus drips off the stent.

Drying and Cross-Linking:

After drying in the drying oven, the stents are placed in a perpendicular position in the UV chamber such that the light can shine into the stent from above and irradiate the same at 500 Watts. Subsequently, excessive not cross-linked PVP is removed by thoroughly rinsing the stent with water.

Example 12

Partial Coating of Stents (d=3 mm)

Solution:
3.2 mg of PU dissolved in 20 ml of N-Methyl-2-pyrrolidone

A spray-coated stent is mounted on an appropriate, freely rotable mold such that it completely abuts the smooth base.

The coating is applied in at least two layers, wherein the solution is absorbed by means of a brush hair and applied onto the region to be coated until the same is completely covered with solution.

Once each area selected for being coated has been filled up until the desired coating thickness has been achieved, the stent is dried at 90° C. After cooling, the stent is detached from the mold.

Example 13

Coating of a Stent Segment with a Small-Meshed Network of Polyether Sulphone Fibers by Means of Electrospinning Solution: 20% per weight of polyether sulphone in methylene chloride The solution is filled into the glass pipette of the electrospinning apparatus. A voltage of 12 kV is applied and the polyether sulphone fiber is applied onto the stent segment to be coated at a flow rate of 3 ml/hr, wherein the distance of the stent is 25 cm and one stent strut after the other is coated.

Example 14

Coating or the Entire Surfaces of a Stent by Interfacial Polycondensation

The mold used for interfacial polycondensation is composed of a rod or pin tapering conically on one end and being flat on the other end, such that the tool can be placed in a stable and upright manner. A thin wire is attached to the tapering end, which is oriented upwardly throughout the coating process, which wire is connected to a lifting device such that the stent can be drawn perpendicularly upward.

The stent is mounted carefully on the adequate mold and placed in the center of the reaction vessel which contains a solution of 15 ml of adipinic acid dichloride in 500 ml of chloroform. The mold must be covered completely by the subjacent solution. Only the thin wire attached to the lifting device sticks out from the vessel. Afterwards, the solution is slowly overcoated with a mixture of 22 g of $\alpha,\omega$-1,6-hexamethylenediamine and 40 g of sodium carbonate in 600 mL of water. The polymer film is formed on the interfacial area. The stent now is slowly and regularly pulled out of the solution such that the thus formed tube can surround the stent. The condensation reaction is stopped by interruption of the upward movement when the coating overlaps the end of the stent by 1 cm. The thus enveloped stent is subsequently rinsed with 50% ethanol, thoroughly washed with water and dried in the drying oven at 30° C.

Example 15

Covalent Coating a Stent with a Heparin Derivative for Conveying Hemocompatible Characteristics to the Stent Surface Non-expanded stents made of medical stainless steel LVM 316 were degreased in the ultrasonic bath with acetone and ethanol and dried at 100° C. in the drying oven. Subsequently, they were dipped into a 2% solution of 3-aminopropyltriethoxysilane in an ethanol/water mixture (50:50: (v/v)) for 5 minutes and dried at 100° C. Subsequently the stents were washed with dematerialized water.

3 mg of desulphated and reacetylated heparin was dissolved at 4° C. in 30 ml of 0.1 M MES buffer (2-(N-Morpholino)ethanesulfonic acid) pH 4.75 and mixed with 30 mg of N-Cyclohexyl-N'-(2-morpholinoethyl)carbodiimide-methyl-p-toluenesulphonate. The stents were stirred at 4° C.

during 15 hours in this solution. Subsequently, they were rinsed with water, 4 M NaCl solution and water for respectively 2 hours.

Example 16

Dip Coating of a Stent with a Silicone Shell for Use as an Ileostomy

A stent mounted on an adequate mold is coated according to example 2 with a commercially available solution of silicone-block polymer (Gelest Sibrid®) dissolved in N-methylpyrrolidone. Subsequently, the solvent is completely removed at 75° C. in the drying oven and the coated stent is carefully detached from the tool using warm water. The overlapping edge is folded as described in example 2 and 3 by wetting with ethanol and THF and connected to the stent.

Example 17

Coating of a Stent with a Silicone Shell

The stent coated according to example 1 is mounted on an adequate mold and spraycoated with a prepolymer silicone dispersion which polycondensates according to the acetoxy crosslinking system (e.g. MED1-6604; MED-6605 or MED6-6606 from NuSil). Prior to that, the dispersion is diluted to a concentration appropriate for spray coating (about 1-2% per weight of polydimethylsiloxane prepolymer in the solvent) by means of an appropriate solvent (e.g. with n-hexane, THF, chloroform, dichloromethane, acetone, ethanol, ether). After the spray coating process, the stent is dried at room temperature and relative air humidity of at least 30% while the polycondensation of the prepolymers takes place by separation of the respective, low molecular carbonic acid, thus forming the silicone shell.

Once the drying process has been completed, the stent coated with silicone is detached from the mold with a small amount of water and subsequently washed with water until the pH of water is achieved.

Example 18

Determination of the Elution Behavior of a Stent Loaded with Active Agent in PBS Buffer Depending on the size of the stent, PBS puffer is poured into a sufficiently small vessel which contains the stent until the same is fully covered with PBS. Afterwards, the vessel is closed with parafilm and incubated in the drying oven at 37° C. After expiration of the selected time intervals, the supernatant is removed by pipetting and the UV absorption thereof is measured at 306 mm.

Example 19

Dip Coating of the Entire Surface of a Stent with a Biodegrable Polymer

The stent spraycoated according to example 1 is mounted on a mold and brought into a 15% per weight polylactide-cloroform dipping solution and coated as described in example 3. Subsequently, the stent is dried in air at room temperature and detached from the mold by wetting with acetone.

Example 20

Spraycoating of the Entire Surfaces of a Stent with a Biodegradable Polymer and an Active Agent The stent spraycoated according to example 1 is mounted on a mold and uniformly sprayed with the rapamycin polylactide glycolide solution from all sides and dried in air at room temperature. This process is repeated at least two times. Subsequently, the completely coated stent is detached from the mold.

Spray Solution:

22 mg of PLGA and 22 mg of rapamycin are weighed out and topped up to 5 g with chloroform.

The invention claimed is:

1. Method for coating the entire surface of lattice-like or mesh-like endoprostheses, wherein in a first coating step the struts of the endoprosthesis which form the lattice-like or mesh-like structure are being covered completely or partially with a polymer coating and in a second coating step the entire surface of the interstices located between the struts which form the lattice-like or mesh-like structure is being coated with a polymer coating, wherein a protruding part is left on both ends, and said protruding part is folded over the edge of the endoprosthesis.

2. Method for coating the entire surface of lattice-like or mesh-like endoprostheses according to claim 1, comprising the following steps:
   a) providing a lattice-like or mesh-like endoprosthesis having a discontinuous surface with interstices between the struts forming the lattice or mesh,
   b) at least partially coating the struts with a polymer A,
   c) wetting the surface of the endoprosthesis coated with the polymer A with an organic solvent,
   d) coating the entire surface of the interstices between the struts which form the lattice-like or mesh-like structure with a polymer coating of a polymer B.

3. Method for coating the entire surface of lattice-like or mesh-like endoprostheses according to claim 1, comprising the following steps:
   a) providing a lattice-like or mesh-like endoprosthesis having a discontinuous surface and comprising struts with an inner surface and an outer surface with interstices between the individual struts,
   b) at least partially coating the inner as well as the outer surface of the struts with a polymer A,
   c) wetting the surface of the endoprosthesis coated with the polymer A with an organic solvent,
   d) coating the entire surface of the inner and/or outer surface as well as of the interstices between the struts with a polymer coating of a polymer B.

4. Method according to claim 2, wherein the coating step b) is performed by spray coating or electrospinning.

5. Method according to claim 2, wherein the interstices between the struts are not being covered with a polymer layer in the coating step b).

6. Method according to claim 2, wherein the wetting according to step c) is performed by dip coating or spray coating.

7. Method according to claim 2, wherein the organic solvent used for the wetting according to step c) contains the polymer B in a concentration lower than that of the polymer B in a solution used for coating according to step d).

8. Method according to claim 2, wherein the polymer A and/or the polymer B are/is selected from the group comprising: polyacrylic acid and polyacrylates such as polymethylmethacrylate, polybutylmethacrylate, polyacrylamide, polyacrylonitriles, polyamides, polyetheramides, polyethylene amine, polyimides, polycarbonates, polycarbourethanes, polyvinyl ketones, polyvinyl halides, polyvinylidene halides, polyvinyl ethers, polyvinylarenes, polyvinyl esters, polyvinyl pyrrollidones, polyoxymethylenes, polyethylene, polypropylene, polytetrafluoro-ethylene, polyurethanes, polyolefine elastomers, polyisobutylenes, EPDM gums, fluorosilicones, carboxymethyl chitosans, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulphones, polyethersulphones, epoxy resins, ABS resins, silicones such as polysiloxanes, polyvinyl halogens and copolymers, cellulose ethers, cellulose triacetates, chitosan, chitosan derivatives, polymerizable oils such as linseed oil and copolymers and/or mixtures thereof.

9. Method according to claim 2, wherein the polymer A and/or the polymer B are/is selected from the group comprising: polyvalerolactones, poly-ε-decalactones, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-one), poly-para-dioxanones, polyanhydrides such as polymaleic acid anhydrides, polyhydroxymethacrylates, fibrin, polycyanoacrylates, polycaprolactone-dimethylacrylates, poly-β-maleic acid, polycaprolactonebutyl-acrylates, multiblock polymers such as from oligocaprolactonedioles and oligodioxanonedioles, polyetherester multiblock polymers such as PEG and poly(butyleneterephthalate), polypivotolactones, polyglycolic acid trimethyl-carbonates, polycaprolactone-glycolides, poly(γ-ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethylcarbonates, polyiminocarbonates, poly(N-vinyl)-pyrrolidone, polyvinylalcohols, polyesteramides, glycolated polyesters, polyphosphoesters, polyphosphazenes, poly[p-carboxyphenoxy)propane], polyhydroxypentanoic acid, polyanhydrides, polyethylene oxide-propylene oxide, soft polyurethanes, polyurethanes with amino acid residues in the backbone, polyetheresters such as polyethylene oxide, polyalkeneoxalates, polyorthoesters as well as copolymers thereof, carrageenanes, fibrinogen, starch, collagen, protein based polymers, polyamino acids, synthetic polyamino acids, zein, modified zein, polyhydroxyalkanoates, pectic acid, actinic acid, modified and unmodified fibrin and casein, carboxymethyl sulphate, albumin, furthermore hyaluronic acid, heparan sulphate, heparin, chondroitine sulphate, dextran, β-cyclodextrins, and copolymers with PEG and polypropylene glycol, gummi arabicum, guar, gelatine, collagen, collagen-N-Hydroxysuccinimide, modifications and copolymers and/or mixtures of the substances mentioned above.

10. Method according to claim 1, wherein the surface of the endoprosthesis is completely covered with a polymer coating by means of dip coating, electro spinning and/or micropippetting.

11. Method according to claim 2, wherein at least one antiproliferative, anti-migration, antiangiogenic, anti-inflammatory, antiphlogistic, cytostatic, cytotoxic and/or anti-thrombotic active agent is applied and/or incorporated beneath, in and/or on the layer of polymer A and/or beneath, in and/or on the layer of polymer B or portions of said layers.

12. Method according to claim 11, wherein the antiproliferative, anti-migration, anti-angiogenic, anti-inflammatory, antiphlogistic, cytostatic, cytotoxic and/or antithrombotic active agent is selected from the group comprising: sirolimus (rapamycin), everolimus, pimecrolimus, somatostatin, tacrolimus, roxithromycin, daunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-Hydroxyoxycyclophosphamide, estramustine, melphalan, ifosfamide, trofosfamide, chlorambucil, bendamustine, dacarbazine, busulfan, procarbazin, treosulfan, temozolomide, thiotepa, Doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, Docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharanthin, 8-α-ergolines, dimethyl ergoline, agroclavin, 1-allyl lisuride, 1-allyl terguride, bromerguride, bromocriptine, elymoclavine, ergocristine, ergocristinine, ergocornine, ergocorninine, ergocryptine, ergocryptinine, ergometrine, ergonovine, ergosine, ergosinine, ergometrinine, ergotamine, ergotaminine, ergovaline, lergotrile, lisuride, lysergol, lysergic acid, lysergic acid amide, lysergic acid diethylamide, isolysergic acid, isolysergic acid amide, isolysergic acid diethylamide, mesulergine, metergoline, methergine, methylergometrine, methysergide, pergolide, proterguride and terguride, celecoxib, thalidomide, Fasudil®, cyclosporine, inhibitor-2ω of SMC proliferation, epothilones A and B, mitoxanthrone, azathioprine, mycophenolate mofetil, c-myc antisense, b-myc antisense, betulinic acid, camptothecin, PI-88 (sulphated oligosaccharide), melanocyte stimulating hormone (α-MSH), activated protein C, IL1-β-Inhibitor, Thymosin α-1, fumaric acid and esters thereof, calcipotriol, tacalcitol, lapachol, β-lapachone, podophyllotoxin, betulin, 2-ethylhydrazide of podophyllic acid, molgramostim (rhuGM-CSF), peginterferon α-2b, lanograstim (r-HuG-CSF), filgrastim, macrogol, dacarbazine, basiliximab, daclizumab, selectin (cytokine antagonist), CETP inhibitor, cadherins, cytokine inhibitors, COX-2-Inhibitor, NFkB, angiopeptin, ciprofloxacin, fluoroblastin, monoclonal antibodies inhibiting the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and sydnonimines, S-nitroso derivatives, tamoxifen, staurosporine, β-estradiol, α-estradiol, estriol, estrone, ethinyl estradiol, fosfestrol, medroxyprogesterone, estradiol cypionates, estradiol benzoates, tranilast, kamebaukarin and other terpenoids applied in the therapy of cancer, verapamil, tyrosine kinase inhibitors (tyrphostines), cyclosporine A, paclitaxel and derivatives thereof such as 6-α-hydroxy-paclitaxel, baccatine, taxotere, macrocyclic oligomers of carbon suboxide (MCS) obtained synthetically and from native sources and derivatives thereof, mofebutazone, acemetacin, diclofenac, lonazolac, dapsone, o-carbamoyl-phenoxyacetic acid, lidocaine, ketoprofen, mefenamic acid, piroxicam, meloxicam, chloroquine phosphate, penicillamine, tumstatin, avastin, D-24851, SC-58125, hydroxychloroquine, auranofin, sodium aurothiomalate, oxaceprol, celecoxib, β-sitosterin, ademetionine, myrtecaine, polidocanol, nonivamide, levomenthol, benzocaine, aescin, ellipticine, D-24851 (Calbiochem), colcemid, cytochalasin A-E, indanocine, nocadazole, protein S 100, bacitracin, vitronectin receptor antagonists, azelastine, guanidyl cyclase stimulator, tissue inhibitor of metal proteinase 1 and 2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF-1, active agents from the group of antibiotics such as cefadroxil, cefazolin, cefaclor, cefoxitin, tobramycin, gentamycin, penicillins such as dicloxacillin, oxacillin, sulfonamides, metronidazole, antithrombotics such as argatroban, aspirin, Abciximab, synthetic antithrombin, bivalirudin, coumadin, enoxoparin, desulphated and N-reacetylated heparin, tissue plasminogen activator, GpIIb/IIIa platelet membrane receptor, factor $X_a$ inhibitor antibody, heparin, hirudin, r-hirudin, PPACK, protamine, sodium salt of 2-methylthiazolidine-2,4-dicarboxylic acid, prourokinase, streptokinase, warfarin, urokinase, vasodilators such as dipyramidole, Trapidil®, nitroprussides, PDGF antagonists such as triazolopyrimidine and seramin, ACE inhibitors such as captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators such as p65, NF-kB or Bcl-xL antisense oligonucleotides, halofuginone, nifedipine, Tocopherol, vitamin B1, B2, B6 and B12, folic acid, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainimide, D24851, SC-58125, retinoic acid, quinidine, disopyrimide, flecamide, propafenone, sotolol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprotozoal agents such as chloroquine, mefloquine, quinine, moreover natural terpenoids such as hippocaesculin, barringtogenol-C21-angelate, 14-Dehydroagrostistachin, agroskerin, agroskerin, agrostistachin, 17-Hydroxyagrostistachin, ovatodiolids, 4,7-oxycycloanisomelic acid, baccharinoids B1, B2, B3 and B7, tubeimoside, bruceanoles A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, moreover cymarin, apocymarin, aristolochic acid, aminopterin, hydroxyanopterin, anemonin, protoanemonin, berberine, cheliburin chloride, cicutoxin, sinococuline combrestatin A and B, cudraisoflavone A, curcumin, dihydronitidine, nitidine chloride, 12-β-hydroxypregnadien-3,20-dione, bilobol, ginkgol, ginkgolic acid, helenalin, indicine, indicine-N-oxide, lasiocarpine, glycoside 1α, justicidin A and B, larreatin, malloterin, mallotochromanol, isobutyrylmallotochromanol, maquiroside A, marchantin A, maytansin, lycoridicin, margetine, pancratistatin, liriodenine, oxoushinsunine, aristolactam-AII, bisparthenolidine, periplocoside A, ursolic acid, deoxypsorospermin, psycorubin, ricin A, sanguinarine, manwu wheat acid, methylsorbifolin, chromones from spathelia, stizophyllin, mansonine, akagerine, dihydrousambaraensine, hydroxyusambarine, strychnopentamine, strychnophylline, usambarine, usambarensine, daphnoretin, lariciresinol, methoxylariciresinol, syringaresinol, umbelliferone, afromoson, acetylvismione B, desacetylvismione A, vismione A and B and sulphurous amino acids such as cystine as well as salts, hydrates, solvates, enantiomers, racemates, enantiomer mixtures, diastereomeric mixtures and mixtures of the above active agents mentioned above.

13. Method according to claim 1, wherein the endoprosthesis to be coated has a tubular, helical and/or braided structure.

14. Method according to claim 1, wherein the endoprosthesis to be coated is a stent, coronary stent, vascular stent, tracheal stent, bronchial stent, urethral stent, esophageal stent, biliary stent, renal stent, stent for use in the small intestine, stent for use in the large intestine, laryngeal implant, bypass, catheter or ileostomy.

15. Endoprosthesis which can be obtained according to claim 1.

16. Endoprosthesis according to claim 15 suited for the prevention, reduction or treatment of stenosis, restenosis, arteriosclerosis, atherosclerosis, vessel occlusions, vessel constrictions, aneurysms, and for artificial openings and accesses.

17. Method according to claim 3, wherein the coating step b) is performed by spray coating or electrospinning.

18. Method according to claim 3, wherein the interstices between the struts are not being covered with a polymer layer in the coating step b).

19. Method according to claim 3, wherein the wetting according to step c) is performed by dip coating or spray coating.

20. Method according to claim 3, wherein the organic solvent used for the wetting according to step c) contains the polymer B in a concentration lower than that of the polymer B in a solution used for coating according to step d).

21. Method according to claim 3, wherein the polymer A and/or the polymer B are/is selected from the group comprising: polyacrylic acid and polyacrylates such as polymethylmethacrylate, polybutylmethacrylate, polyacrylamide, polyacrylonitriles, polyamides, polyetheramides, polyethylene amine, polyimides, polycarbonates, polycarbourethanes, polyvinyl ketones, polyvinyl halides, polyvinylidene halides, polyvinyl ethers, polyvinylarenes, polyvinyl esters, polyvinyl pyrrollidones, polyoxymethylenes, polyethylene, polypropylene, polytetrafluoro-ethylene, polyurethanes, polyolefine elastomers, polyisobutylenes, EPDM gums, fluorosilicones, carboxymethyl chitosans, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulphones, polyethersulphones, epoxy resins, ABS resins, silicones such as polysiloxanes, polyvinyl halogens and copolymers, cellulose ethers, cellulose triacetates, chitosan, chitosan derivatives, polymerizable oils such as linseed oil and copolymers and/or mixtures thereof.

22. Method according to claim 3, wherein the polymer A and/or the polymer B are/is selected from the group comprising: polyvalerolactones, poly-ϵ-decalactones, polylactides, polyglycolides, copolymers of the polylactides and polyglycolides, poly-ϵ-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-one), poly-para-dioxanones, polyanhydrides such as polymaleic acid anhydrides, polyhydroxymethacrylates, fibrin, polycyanoacrylates, polycaprolactone-dimethylacrylates, poly-β-maleic acid, polycaprolactonebutyl-acrylates, multiblock polymers such as from oligocaprolactonedioles and oligodioxanonedioles, polyetherester multiblock polymers such as PEG and poly(butyleneterephthalate), polypivotolactones, polyglycolic acid trimethyl-carbonates, polycaprolactone-glycolides, poly(γ-ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethylcarbonates, polyiminocarbonates, poly(N-vinyl)-pyrrolidone, polyvinylalcohols, polyesteramides, glycolated polyesters, polyphosphoesters, polyphosphazenes, poly[p-carboxyphenoxy)propane], polyhydroxypentanoic acid, polyanhydrides, polyethylene oxide-propylene oxide, soft polyurethanes, polyurethanes with amino acid residues in the backbone, polyetheresters such as polyethylene oxide, polyalkeneoxalates, polyorthoesters as well as copolymers thereof, carrageenanes, fibrinogen, starch, collagen, protein based polymers, polyamino acids, synthetic polyamino acids, zein, modified zein, polyhydroxyalkanoates, pectic acid, actinic acid, modified and unmodified fibrin and casein, carboxymethyl sulphate, albumin, furthermore hyaluronic acid, heparan sulphate, heparin, chondroitine sulphate, dextran, β-cyclodextrins, and copolymers with PEG and polypropylene glycol, gummi arabicum, guar, gelatine, collagen, collagen-N-Hydroxysuccinimide, modifications and copolymers and/or mixtures of the substances mentioned above.

23. Method according to claim 2, wherein the surface of the endoprosthesis is completely covered with a polymer coating by means of dip coating, electrospinning and/or micropippetting.

24. Method according to claim 3, wherein the surface of the endoprosthesis is completely covered with a polymer coating by means of dip coating, electrospinning and/or micropippetting.

25. Method according to claim 3, wherein at least one antiproliferative, anti-migration, antiangiogenic, anti-inflammatory, antiphlogistic, cytostatic, cytotoxic and/or anti-thrombotic active agent is applied and/or incorporated beneath, in and/or on the layer of polymer A and/or beneath, in and/or on the layer of polymer B or portions of said layers.

26. Method according to claim 25, wherein the antiproliferative, anti-migration, anti-angiogenic, anti-inflammatory, antiphlogistic, cytostatic, cytotoxic and/or antithrombotic active agent is selected from the group comprising: sirolimus (rapamycin), everolimus, pimecrolimus, somatostatin, tacrolimus, roxithromycin, daunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-Hydroxyoxycyclophosphamide, estramustine, melphalan, ifosfamide, trofosfamide, chlorambucil, bendamustine, dacarbazine, busulfan, procarbazin, treosulfan, temozolomide, thiotepa, Doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, Docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharanthin, 8-α-ergolines, dimethyl ergoline, agroclavin, 1-allyl lisuride, 1-allyl terguride, bromerguride, bromocriptine, elymoclavine, ergocristine, ergocristinine, ergocornine, ergocorninine, ergocryptine, ergocryptinine, ergometrine, ergonovine, ergosine, ergosinine, ergometrinine, ergotamine, ergotaminine, ergovaline, lergotrile, lisuride, lysergol, lysergic acid, lysergic acid amide, lysergic acid diethylamide, isolysergic acid, isolysergic acid amide, isolysergic acid diethylamide, mesulergine, metergoline, methergine, methylergometrine, methysergide, pergolide, proterguride and terguride, celecoxib, thalidomide, Fasudil®, cyclosporine, inhibitor-2ω of SMC proliferation, epothilones A and B, mitoxanthrone, azathioprine, mycophenolate mofetil, c-myc antisense, b-myc antisense, betulinic acid, camptothecin, PI-88 (sulphated oligosaccharide), melanocyte stimulating hormone (α-MSH), activated protein C, IL1-β-Inhibitor, Thymosin α-1, fumaric acid and esters thereof, calcipotriol, tacalcitol, lapachol, β-lapachone, podophyllotoxin, betulin, 2-ethylhydrazide of podophyllic acid, molgramostim (rhuGM-CSF), peginterferon α-2b, lanograstim (r-HuG-CSF), filgrastim, macrogol, dacarbazine, basiliximab, daclizumab, selectin (cytokine antagonist), CETP inhibitor, cadherins, cytokine inhibitors, COX-2-Inhibitor, NFkB, angiopeptin, ciprofloxacin, fluoroblastin, monoclonal antibodies inhibiting the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and sydnonimines, S-nitroso derivatives, tamoxifen, staurosporine, β-estradiol, α-estradiol, estriol, estrone, ethinyl estradiol, fosfestrol, medroxyprogesterone, estradiol cypionates, estradiol benzoates, tranilast, kamebaukarin and other terpenoids applied in the therapy of cancer, verapamil, tyrosine kinase inhibitors (tyrphostines), cyclosporine A, paclitaxel and derivatives thereof such as 6-α-hydroxy-paclitaxel, baccatine, taxotere, macrocyclic oligomers of carbon suboxide (MCS) obtained synthetically and from native sources and derivatives thereof, mofebutazone, acemetacin, diclofenac, lonazolac, dapsone, o-carbamoyl-phenoxyacetic acid, lidocaine, ketoprofen, mefenamic acid, piroxicam, meloxicam, chloroquine phosphate, penicillamine, tumstatin, avastin, D-24851, SC-58125, hydroxychloroquine, auranofin, sodium aurothiomalate, oxaceprol, celecoxib, β-sitosterin, ademetionine, myrtecaine, polidocanol, nonivamide, levomenthol, benzocaine, aescin, ellipticine, D-24851 (Calbiochem), colcemid, cytochalasin A-E, indanocine, nocadazole, protein S 100, bacitracin, vitronectin receptor antagonists, azelastine, guanidyl cyclase stimulator, tissue inhibitor of metal proteinase 1 and 2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF-1, active agents from the group of antibiotics such as cefadroxil, cefazolin, cefaclor, cefoxitin, tobramycin, gentamycin, penicillins such as dicloxacillin, oxacillin, sulfonamides, metronidazole, antithrombotics such as argatroban, aspirin, Abciximab, synthetic antithrombin, bivalirudin, coumadin, enoxoparin, desulphated and N-reacetylated heparin, tissue plasminogen activator, GpIIb/IIIa platelet membrane receptor, factor $X_a$ inhibitor antibody, heparin, hirudin, r-hirudin, PPACK, protamine, sodium salt of 2-methylthiazolidine-2,4-dicarboxylic acid, prourokinase, streptokinase, warfarin, urokinase, vasodilators such as dipyramidole, Trapidil®, nitroprussides, PDGF antagonists such as triazolopyrimidine and seramin, ACE inhibitors such as captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators such as p65, NF-kB or Bcl-xL antisense oligonucleotides, halofuginone, nifedipine, Tocopherol, vitamin B1, B2, B6 and B12, folic acid, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainimide, D24851, SC-58125, retinoic acid, quinidine, disopyrimide, flecamide, propafenone, sotolol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprotozoal agents such as chloroquine, mefloquine, quinine, moreover natural terpenoids such as hippocaesculin, barringtogenol-C21-angelate, 14-Dehydroagrostistachin, agroskerin, agroskerin, agrostistachin, 17-Hydroxyagrostistachin, ovatodiolids, 4,7-oxycycloanisomelic acid, baccharinoids B1, B2, B3 and B7, tubeimoside, bruceanoles A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, moreover cymarin, apocymarin, aristolochic acid, aminopterin, hydroxyanopterin, anemonin, protoanemonin, berberine, cheliburin chloride, cicutoxin, sinococuline combrestatin A and B, cudraisoflavone A, curcumin, dihydronitidine, nitidine chloride, 12-β-hydroxypregnadien-3,20-dione, bilobol, ginkgol, ginkgolic acid, helenalin, indicine, indicine-N-oxide, lasiocarpine, glycoside 1α, justicidin A and B, larreatin, malloterin, mallotochromanol, isobutyrylmallotochromanol, maquiroside A, marchantin A, maytansin, lycoridicin, margetine, pancratistatin, liriodenine, oxoushinsunine, aristolactam-AII, bisparthenolidine, periplocoside A, ursolic acid, deoxypsorospermin, psycorubin, ricin A, sanguinarine, manwu wheat acid, methylsorbifolin, chromones from spathelia, stizophyllin, mansonine, akagerine, dihydrousambaraensine, hydroxyusambarine, strychnopentamine, strychnophylline, usambarine, usambarensine, daphnoretin, lariciresinol, methoxylariciresinol, syringaresinol, umbelliferone, afromoson, acetylvismione B, desacetylvismione A, vismione A and B and sulphurous amino acids such as cystine as well as salts, hydrates, solvates, enantiomers, racemates, enantiomer mixtures, diastereomeric mixtures and mixtures of the above active agents mentioned above.

27. Method according to claim 2, wherein the endoprosthesis to be coated has a tubular, helical and/or braided structure.

28. Method according to claim 3, wherein the endoprosthesis to be coated has a tubular, helical and/or braided structure.

29. Method according to claim 2, wherein the endoprosthesis to be coated is a stent, coronary stent, vascular stent, tracheal stent, bronchial stent, urethral stent, esophageal stent, biliary stent, renal stent, stent for use in the small intestine, stent for use in the large intestine, laryngeal implant, bypass, catheter or ileostomy.

30. Method according to claim 3, wherein the endoprosthesis to be coated is a stent, coronary stent, vascular stent, tracheal stent, bronchial stent, urethral stent, esophageal stent, biliary stent, renal stent, stent for use in the small intestine, stent for use in the large intestine, laryngeal implant, bypass, catheter or ileostomy.

31. Endoprosthesis which can be obtained according to claim 2.

32. Endoprosthesis which can be obtained according to claim 3.

33. Endoprosthesis according to claim 31 suited for the prevention, reduction or treatment of stenosis, restenosis, arteriosclerosis, atherosclerosis, vessel occlusions, vessel constrictions, aneurysms, and for artificial openings and accesses.

34. Endoprosthesis according to claim 32 suited for the prevention, reduction or treatment of stenosis, restenosis, arteriosclerosis, atherosclerosis, vessel occlusions, vessel constrictions, aneurysms, and for artificial openings and accesses.

* * * * *